United States Patent
Granzotto et al.

(10) Patent No.: US 6,757,392 B1
(45) Date of Patent: Jun. 29, 2004

(54) ELECTRONIC STETHOSCOPE

(76) Inventors: Artemio Granzotto, Hardturmstrasse 135, 8005 Zürich (CH); Fridolin Voegeli, CADItec AG Euro 1, 6343 Rotkreuz (CH)

(*) Notice: Subject to any disclaimer, the term of this patent is extended or adjusted under 35 U.S.C. 154(b) by 0 days.

(21) Appl. No.: 09/003,054

(22) PCT Filed: Jun. 17, 1996

(86) PCT No.: PCT/CH96/00230
§ 371 (c)(1),
(2), (4) Date: Feb. 26, 1999

(87) PCT Pub. No.: WO97/01987
PCT Pub. Date: Jan. 23, 1997

(30) Foreign Application Priority Data
Jul. 6, 1995 (CH) .............................. 1968/98

(51) Int. Cl.[7] .............................. A61B 7/04; A61B 7/02; A61B 5/04; A61B 5/02
(52) U.S. Cl. .................. 381/67; 181/131; 600/528; 600/393; 600/509; 600/513
(58) Field of Search .................. 381/67; 181/131; 600/528, 393, 509, 508; 422/44; 425/542

(56) References Cited

U.S. PATENT DOCUMENTS

| | | | | |
|---|---|---|---|---|
| 3,858,005 A | * | 12/1974 | Marshall et al. | 381/67 |
| 4,181,122 A | * | 1/1980 | Ueda | 181/171 |
| 4,254,302 A | * | 3/1981 | Walshe | 381/67 |
| 4,350,164 A | * | 9/1982 | Allain, Jr. | 600/383 |
| 4,362,164 A | * | 12/1982 | Little et al. | 381/67 |
| 4,638,807 A | * | 1/1987 | Ryder | 600/383 |
| 5,002,625 A | * | 3/1991 | Naritomi et al. | 156/245 |
| 5,003,605 A | * | 3/1991 | Phillipps et al. | 381/67 |
| 5,029,590 A | * | 7/1991 | Allain et al. | 600/523 |
| 5,139,021 A | * | 8/1992 | Sekii et al. | 128/908 |
| 5,218,969 A | * | 6/1993 | Bredesen et al. | 381/67 |

* cited by examiner

Primary Examiner—Minsun Oh Harvey
Assistant Examiner—Andrew Graham
(74) Attorney, Agent, or Firm—Ann W. Speckman; Janet Sleath

(57) ABSTRACT

An electronic stethoscope comprises a headpiece, a chest-piece and two earpieces. The headpiece is fitted with a display arrangement in the form of a liquid-crystal display. A microphone, one or more sensors and fixed electrodes and movable electrodes are mounted in the headpiece. The movable electrodes are fixed to pivoted arms which form a contact ring.

9 Claims, 3 Drawing Sheets

ELECTRONIC STETHOSCOPE

FIELD OF THE INVENTION

The present invention concerns a multifunctional stethoscope usable on both ears and preferably fitted with a bow.

BACKGROUND OF THE INVENTION

Stethoscopes are instruments for investigating sound phenomena or for auscultation of organ functions. Stethoscopes commonly in use are tube stethoscopes usable on both ears and fitted with bows; as the head-piece they have an open bell or a part closed by a membrane. In addition to mechanical tube stethoscopes, electronic stethoscopes are also available on the market. By the head-piece of a stethoscope is meant a listening spout which can be placed on the body of the patient being examined. The listening spout connected to a chest-piece from which two bow sections lead to the ears.

Whereas in the case of the tube stethoscope the acoustic signals are conducted directly from the spout placed on the body via the chest-piece and the two bow sections to the ears of the examining doctor, with the electronic stethoscope the acoustic signals are received by a microphone fitted to the head-piece, converted into electric signals, transmitted to loudspeakers at the ears and amplified there.

In addition to traditional electronic stethoscopes, special models are also known for phonocardiography. A phonocardio-graphically operating stethoscope is known, for example, from U.S. Pat. No. 4,840,183. A further phonocardiographic stethoscope which is connectable to suitable graphic recording units is described in U.S. Pat. No. 5,025,809.

Whereas in the case of stethoscopes operating phonocardiographically, heart noises caused by heart functioning are received and amplified and, if required, recorded by suitable means, electrocardiographs plot the curve structure in terms of the temporal progression of the bio-electric voltages accompanying the increase and decrease of excitation within the heart.

These bio-electric voltages are transmitted by means of electrodes attached to the body surface. The data acquired, displayed in a time sequence, forms an electrocardiogram (ECG) which shows several diagnostically relevant factors.

Finally, an oesophageal stethoscope is known from U.S. Pat. No. 5,394,880; this has a catheter which can be inserted into the oesophagus, within which catheter a cardiophonically operating microphone and several sensors are fitted. In particular, a sensor for measuring body temperature and two electrodes for electrocardiographic recording are provided here. The signals received through the catheter are transmitted via an electric lead to a plug socket which enables connection to suitable recording devices.

Whereas traditional electronic stethoscopes and known electrocardiographs are instruments which are in daily use by general practitioners, oesophageal stethoscopes are highly sensitive instruments which are used only in the clinical context.

SUMMARY OF THE INVENTION

It is the object of the present invention to provide a multifunctional stethoscope which can be used in a mobile way by the general practitioner, and which allows simple electrocardiographic investigations to be made in addition to auscultation.

This objective is met by an electronic stethoscope with a headpiece in which several sensors are arranged around the microphone, at least three of which are electrodes positioned in an Einthoven Triangle arrangement in order to obtain an electrocardiogram (ECG), and in which a display arrangement is incorporated in the headpiece for visual display of body function values obtained by the sensors, the values being collected by an evaluation unit and processed for the display arrangement.

An optimally space- and weight-saving solution is achieved if the display arrangement located in the headpiece takes the form of a liquid-crystal display. The cheapest solution is achieved if the three electrodes for obtaining the ECG are fixed inside the head-piece.

If only one of the three electrodes is fixed inside the head-piece while the two other electrodes are attached movably on the stethoscope head-piece, the Einthoven Triangle can be altered or enlarged. The greatest possibility of variation is achieved if all three of the electrodes used to obtain the ECG are made movable.

An especially preferred embodiment has the movable electrodes mounted pivotably in arms fitted to the periphery of the contact surface of the stethoscope head. In the position where they are not pivoted out they form a closed contact ring. This allows a relatively large Einthoven Triangle for the electrodes to be formed despite the use of a relatively small stethoscope head. It also yields a correspondingly informative ECG. This latter solution can be further improved by forming the pivoted arms so that they are in electrical contact with the evaluation unit only in the swiveled-out position. This prevents relatively uninformative data with regard to production of an ECG from being recorded.

The traditional stethoscope, known for approx. the last 100 years, has become the most-used diagnostic instrument of doctors because it can be used easily, conveniently and without preparation, can be always carried in the pocket or around the neck, and used without loss of time. All other instruments are separate, usually electrical devices which take up space and have to be set up, etc.

The electronic stethoscope according to the invention enlarges the previous, simple possibilities of (acoustic) diagnosis by simultaneously capturing, with equal simplicity, visually displaying and evaluating the bioelectrical excitation involved in heart activity. In this way important information on irregularities in heart frequency, so-called tachycardiae, ventricle flicker and other problems otherwise only detectable later, can be recognized straight away at the first medical examination.

The electronic stethoscope according to the invention can additionally be fitted with sensors for measuring blood pressure and/or temperature. The evaluation unit, also mounted in the headpiece, normally transmits the signals directly to the recording device. However, the signals can also be input into a data memory and only from there transmitted to a static image on the display device.

BRIEF DESCRIPTION OF THE DRAWINGS

In the following description one embodiment of the object according to the invention is described with the aid of the attached drawings.

DETAILED DESCRIPTION

Figure 1:
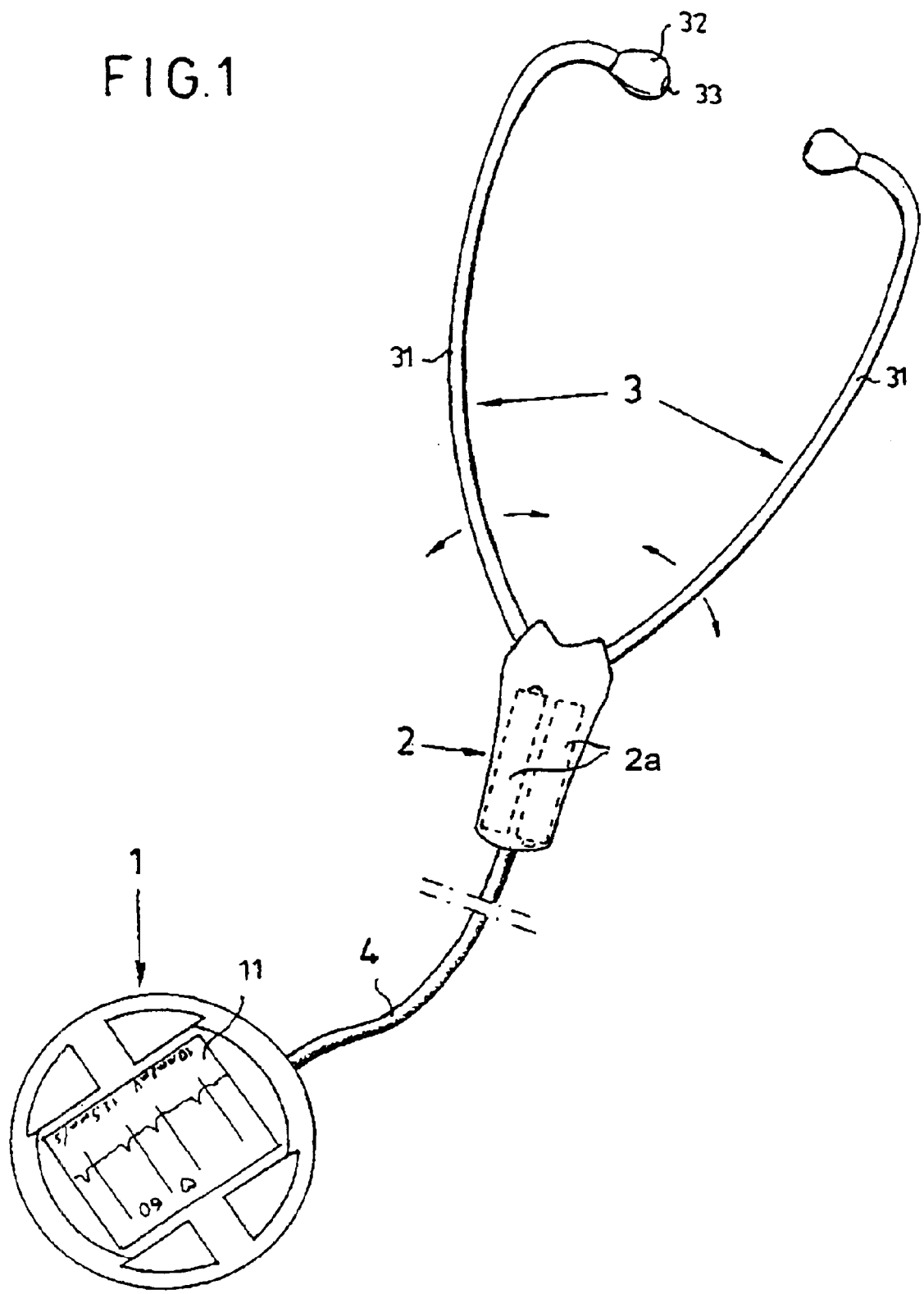
FIG. 1 shows a general view of the electronic stethoscope.

The electronic stethoscope according to the invention has the same general structure as a conventional tube stethoscope. It has a stethoscope head or headpiece 1 to be placed on the patient; this is connected to the so-called chest-piece by a connecting lead 4. The two earpieces 3 are connected to the chest-piece 2.

Inside the chest-piece 2 is mounted the feed source 2a, which is formed as a plastic housing. The feed source comprises one or more batteries or accumulators which can preferably be recharged. The two earpieces 3 are connected to the chest-piece 2. Each earpiece includes a bow 31 which is connected by a flexible joint to the chest-piece 2. An olive-shaped part 32 with a sound aperture 33 is fitted to the end of each bow 31. Within each 'olive' 32 a loudspeaker is mounted.

The embodiment of the electronic stethoscope according to the invention is limited essentially to the structure of the stethoscope head 1. The most essential feature of this stethoscope head lies in the integrated display arrangement 11. The display arrangement 11 is formed here as a liquid crystal display. The display arrangement 11 has various display fields 12 which can be activated by pressing the operating keys 13. For example, the display fields 12 can show heart rate, body temperature or an ECG. In the corresponding fields 12 criteria for evaluating the ECG displayed are also shown. From the information shown here it can be seen that a peak height of 10 mm corresponds to one mV.

Figure 2:
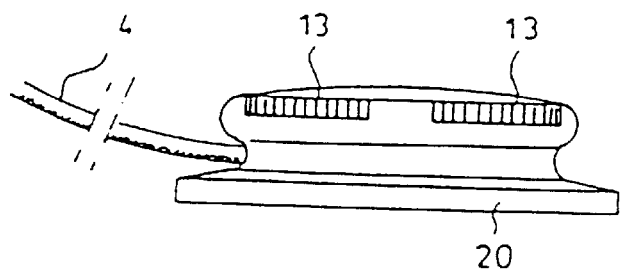
FIG. 2 shows a side view of the headpiece of the same stethoscope.
Figure 3:
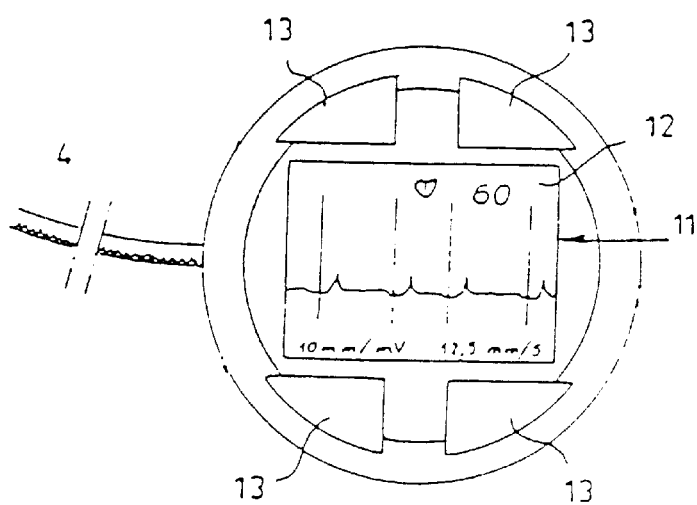
FIG. 3 shows a top view of the headpiece of the stethoscope according to FIG. 2.

The progression on the X axis is also shown. In the example illustrated 12.5 mm corresponds to one second. In the side view in FIG. 2 a contact ring 20 can also be seen; this provides the contact surface to the patient.

Figure 4:
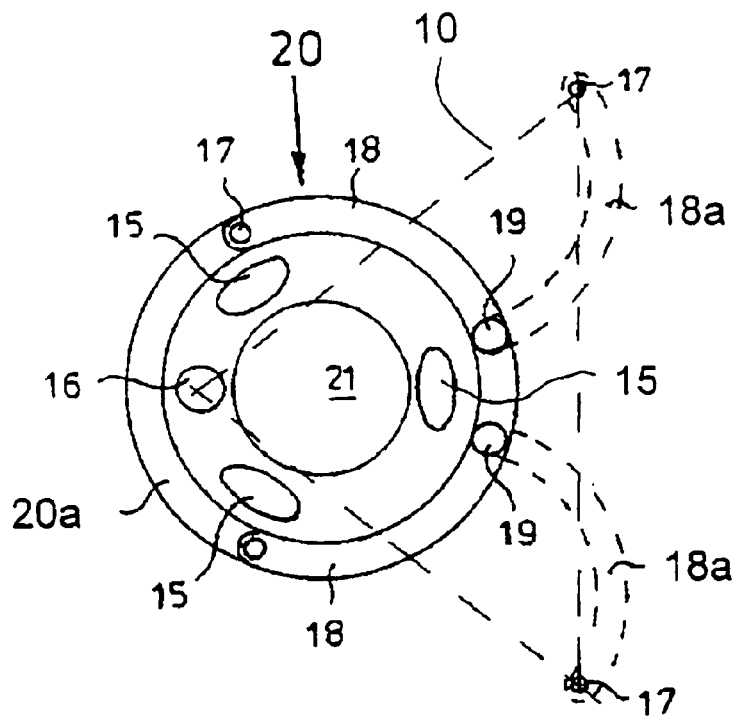
FIG. 4 shows a bottom view of the headpiece of the electronic stethoscope when in use and FIG. 5 shows the bottom view of a variant of the stethoscope head.
Figure 5:
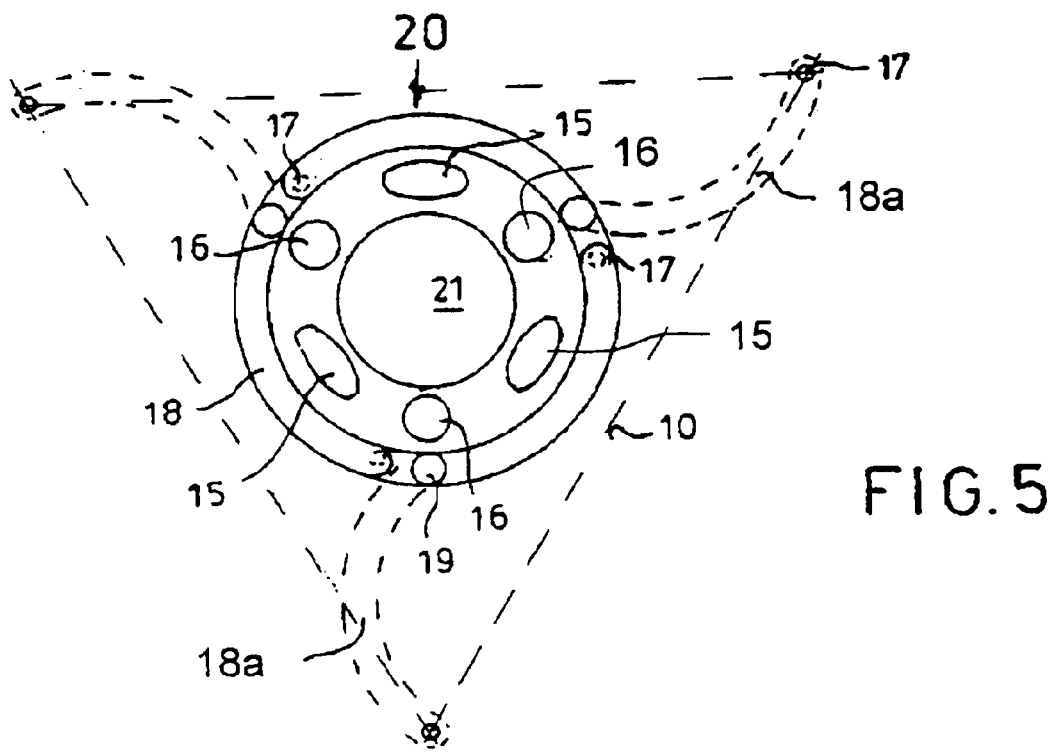

If one looks at the view of the contact surface shown in FIGS. 4 and 5, the operative parts can be seen. At the center of the stethoscope head 1 is the microphone 21. This is set back inwardly from the contact surface formed by the contact ring 20 so that the microphone does not rest directly on the skin. However, it is possible, as with known electronic stethoscopes, to provide this microphone with a membrane which is aligned at least very close to the level of the contact ring 20 so that it rests on the body surface of the patient. The contact ring is normally several millimeters thick, so that it encloses a resonance chamber. In the embodiment according to FIG. 4, the contact ring is made up of three parts. About one-third of the contact ring 20 consists of a ring section 20a fixed to the stethoscope head 1, while the two other sections of the contact ring are formed as arc-shaped arms 18 which can be swiveled outwards about the pivot joints 19.

One electrode 16 is mounted inside the stethoscope head, while the two other, movable electrodes 17, used to obtain an ECG, are fixed to the ends of the arms 18. In addition to the three electrodes 16, 17, three sensors 15 are also fitted to the stethoscope head 1. These sensors 15 are aligned substantially in the plane of the surface of the contact ring 20. These sensors can be used to obtain other information reflecting body functioning. For example, one or more sensors can be used to measure body temperature, or one or more sensors can be used to measure blood pressure.

A stethoscope according to FIG. 4 is therefore multifunctional. As long as the arms 18 are not swiveled out, they form the contact ring 20 with the contact ring part 20a, and thus enclose a resonance chamber which can be used for auscultation of various body functions. With the arms 18 in this position the microphone 21 can also be used to record a phonocardiogram. By contrast, it is necessary to swivel the arms 18 into position 18a in order to record an electrocardiogram. In the swiveled-out position the fixed electrode 16 and the movable electrodes 17 on the swiveled-out arms 18a form a so-called Einthoven Triangle 10.

To avoid erroneous signals, it can be an advantage for the pivot joints 19 to be connected by switching contacts with the effect that an electrical connection between the electrodes 17 and the evaluation unit is made only if the arms 18 are in the correct fully swiveled-out position 18a.

In the embodiment according to FIG. 5 the stethoscope head is modified so that on one hand three fixed electrodes 16 are fitted, and, further, the contact ring 20 is formed of three movable arms. In this case, too, a movable electrode 17 is fitted to the end of each arm 18 furthest from the pivot joint 19. In this case the electrodes 16 or 17 are switched so that in the non-swiveled-out position of arms 18 only the fixed electrodes 16 operate, whereas after the arms 18 are swiveled out to position 18a only the movable electrodes 17 operate. This arrangement provides a significantly larger Einthoven Triangle 10.

Figure 6:
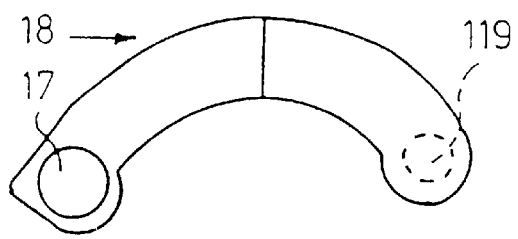
FIG. 6 shows a top view of a special designed bow-formed arm with its electrode and FIG. 7 shows a side view of the same arm.
Figure 7:
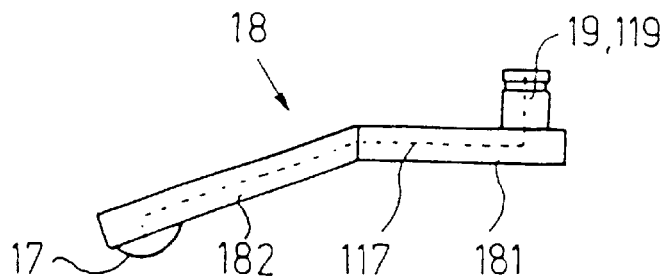

To achieve a firm contact of the electrodes 17 arranged at the movable arms 18 on the body of a patient, it is of advantage for the arms 18 to be flexible. Such an improved embodiment of a swivable arm is shown in FIGS. 6 and 7. In principle such arms could be made in two parts which could be hingeably connected with each other. However, such an arrangement might cause problems when the stethoscope has to be disinfected. Therefore the arm 18 is preferably manufactured in a single piece and injection molded in two stages with two different plastics whereas the electrical parts, namely the sensor 17 and the plug contact 119 that forms at the same time the pivot joint 19 are together with the conducting connection 117 imbedded in the so molded arm. For the injection molded arm-part 181 on which the pivot joint 19 is arranged a harder (less flexible) plastic is selected than for the other arm-part 182 on which the sensor 17 is arranged. This arm-part 182 is molded with a softer (more flexible) plastic. Both arm-parts incline at an obtuse angle which changes under pressure on the stethoscope-head.

The electronic components needed for such a stethoscope are available on the market. Their programming must be optimized for this application.

The corresponding electronics include essentially a digital-analog converter, amplifier, clock generator for timing and preferably a memory unit in which the measurement results can be temporarily stored and can be called up for display on the display arrangement. In this way a static ECG image can be recorded, which can be studied more closely for diagnosis.

What is claimed is:

1. An electronic stethoscope comprising a headpiece connected to a chest-piece by means of a lead, and two earpieces connected to the chest-piece, wherein the headpiece comprises:

(a) at least three electrodes for obtaining an electrocardiogram (ECG);

(b) a display arrangement for visual display of body function values obtained by the electrodes; and (c) an evaluation unit for collection and processing of the body function values for displaying at the display arrangement, wherein at least two of the three electrodes are fixed to arms attached pivotably to a periphery of a contact surface of the headpiece, the arms being adapted for swiveling out and forming at least approximately a closed contact ring when in a non-swivelled-out position, and wherein the three electrodes are positionable to form an approximately Einthoven triangle arrangement in a swiveled-out position.

2. An electronic stethoscope according to claim 1, wherein the display arrangement is a liquid-crystal display.

3. An electronic stethoscope according to claim 1, wherein the pivotable arms are flexible.

4. An electronic stethoscope according to claim 3, wherein each of the flexible arms are formed of two connected arm-pieces which are made of two different plastics having two different flectional elasticity properties.

5. An electronic stethoscope according to claim 1, wherein each of the earpieces has a loudspeaker mounted therein and the headpiece comprises a microphone.

6. An electronic stethoscope according to claim 1, wherein one of the three electrodes is mounted at a fixed position in the headpiece.

7. An electronic stethoscope according to claim 1, comprising three movable electrodes and three electrodes mounted in a fixed position in the headpiece.

8. An electronic stethoscope according to claim 1, wherein a switch is provided for electrically connecting the movable electrodes to the evaluation unit only when in a swiveled-out position.

9. An electronic stethoscope according to claim 1, further comprising at least one sensor selected from the group consisting of:

(a) sensors for measurement of blood pressure; and (b) sensors for measurement of blood temperature.

* * * * *